United States Patent
Kunofsky

Patent Number: 5,111,850
Date of Patent: May 12, 1992

[54] BODY RESTRAINING DEVICE

[76] Inventor: Morris I. Kunofsky, 6010 Royalcrest, Dallas, Tex. 75230

[21] Appl. No.: 567,292

[22] Filed: Aug. 14, 1990

[51] Int. Cl.⁵ ................................................ A61F 5/37
[52] U.S. Cl. .................................... 128/873; 128/846; 128/869; 128/870
[58] Field of Search ................ 128/873, 846, 869, 870

[56] References Cited

U.S. PATENT DOCUMENTS

| | | | |
|---|---|---|---|
| 1,653,815 | 12/1927 | Millar | 128/873 |
| 2,664,083 | 12/1953 | Heymans | 128/873 |
| 2,948,278 | 8/1960 | Topa | 128/873 |
| 3,547,079 | 12/1970 | Bassett | 128/873 X |
| 4,485,806 | 12/1984 | Akers | 128/873 X |
| 4,524,768 | 6/1985 | Serrao | 128/873 |
| 4,790,040 | 12/1988 | Grilliot et al. | 5/413 |
| 4,895,171 | 1/1990 | Onik | 128/846 |

Primary Examiner—Robert A. Hafer
Assistant Examiner—Kerry Owens
Attorney, Agent, or Firm—Daniel Rubin

[57] ABSTRACT

A body restraining device for physically restraining an individual and comprised of a foraminous shroud defined by an elongated length and tubular section having the upper shroud end closed and the lower shroud end open. The shroud is preferably comprised of a high-strength netting material such that drawing the open end downward over the head of an erect person to past the feet, effectively restrains the person against injurious movement. Once the shroud is in place, the restrained person can easily be forced into a bent posture enabling the shroud ends to be knotted together for securing the restraint device. Strap means are provided for maintaining the shroud in a collapsed position in readiness for subsequent use.

7 Claims, 2 Drawing Sheets

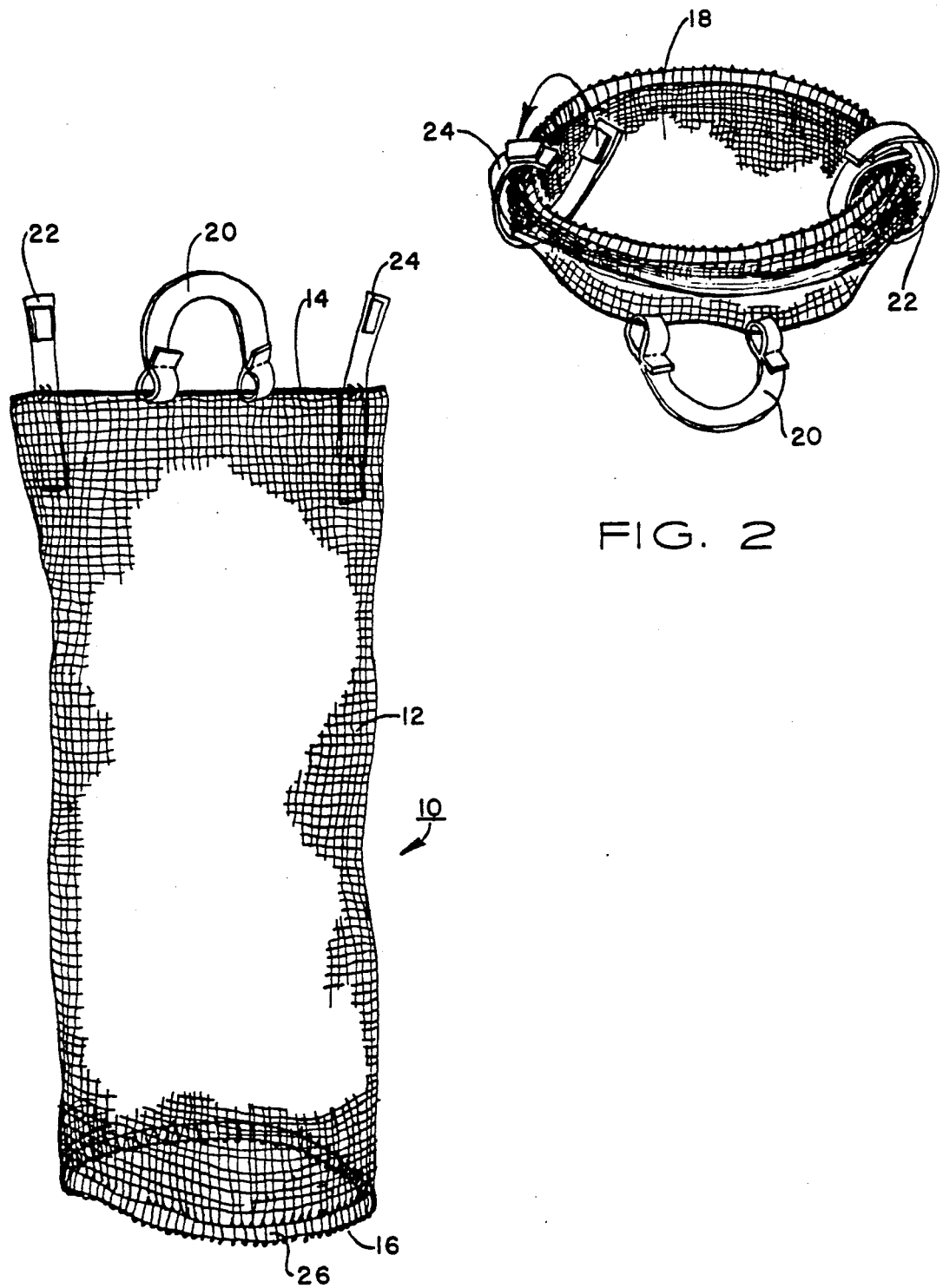

BODY RESTRAINING DEVICE

FIELD OF THE INVENTION

The field of art to which the invention relates comprises the art of devices for physically restraining individuals exhibiting or likely to exhibit violent behavior.

BACKGROUND OF THE INVENTION

Within our society there is a segment of individuals prone to violent behavior. Whether it be persons who are mentally disturbed, persons under arrest or otherwise normal persons subject to temporary emotional conflict, it is frequently necessary to restrain such persons physically against behavioral violence. The purpose of the restraint is not only to protect those persons against self-inflicted injury, but also to protect surrounding properties and other persons in responsible charge of the affected individual. In the absence of a restraint being applied, it is frequently difficult to deal with and manage the physical behavior of the individual.

BACKGROUND OF THE PRIOR ART

Devices for physically restraining individuals have been used since time immemorial. Such devices include hog-tying, handcuffs, straitjackets, blanket wraps, etc., that have long been used to physically restrain individuals. Which of these is selected depends both on what is available at the time and the circumstances of the situation. During an arrest, for example, the arresting law enforcement officer may use handcuffs and/or hog-tying to restrain both the hands and/or feet of the arrested individual.

It will be appreciated that applying handcuffs or hog-tying in an arresting situation where persons to be restrained may resist arrest by arm flailing, kicking, or other violent movements, can prove most difficult. Indeed, a high level of manual restraint against the arrested individual is frequently required of the arresting officer before handcuffing and/or hog-tying can be completed. In hog-tying, the hands and feet are typically attached from behind, causing the individual's back to be bent backward and from which frequent back injuries are known to result.

The straitjacket is more commonly used in mental institutions but does not restrain the feet. Moreover, applying the straitjacket can be difficult in that it requires some cooperation from the recipient to allow arm insertion into the respective sleeves. Because of the difficulties in applying the straitjacket, shoulder injuries frequently result while in any event the individual without any feet restraint continues able to kick or run.

Blanket wrapping or a conventional net can be worked loose by the individual and likewise leaves the feet unrestrained so as to enable the individual to kick and/or run.

OBJECTS OF THE INVENTION

It is an object of the invention to effect a novel device for physically restraining individuals prone or potentially prone to violent behavior.

It is a further object of the invention to provide the previous object with a device more easily applied to restrain an individual without the attendant injuries or escape possibilities associated with similar purpose devices of the prior art.

It is a still further object of the invention to provide a restraining device in accordance with the previous objects that is more completely effective in physically restraining an individual without the necessity of separate restraints applied to the hands and/or legs.

SUMMARY OF THE INVENTION

This invention relates to a device for physically restraining an individual against deleterious limb movement. More specifically, the invention relates to a device capable of more easily and more quickly restraining an individual under circumstances in which resistance to being restrained can be anticipated. When applying the device hereof, physical restraint is so immediately complete as to promptly eliminate any significant resistance in the form of arm flailing, feet kicking, etc. Not only is the individual restrained but the individual is rendered readily portable without concern of escape and without the attendant injuries previously known to occur. The advantage in the fields of law enforcement, mental health, etc., should instantly apparent.

The foregoing is achieved by means of a restraining device in accordance with the invention comprised of an elongated tubular shaped netting formed as a foraminous shroud closed at one end and open at the other. The netting per se is of extremely high-strength and formed tubular on the order of 7-8 feet in length. Being closed at one end and defining an internal cavity devised to capture a person weighing in excess of 300 pounds, the open end of the shroud can be easily drawn down over the individual. Once the individual is covered head to feet, the open end can be drawn together and optionally tied such that the disposed individual becomes caged and prevented from harmful movement. At that point, with or without tying, the open end can be tugged so as to readily force the individual into a bending posture before the open shroud end is drawn together and knotted about itself or to the closed end. When wrapped in this manner, the disposed individual, with or without the hands or feet being bound, is unable to move feet or legs beyond the physical restraint of the shroud and is therefore rendered essentially helpless.

The above noted features and advantages of the invention as well as other superior aspects thereof will be further appreciated by those skilled in the art upon reading the detailed description which follows in conjunction with the drawings.

BRIEF DESCRIPTION OF THE DRAWINGS

FIG. 1 is an isometric view of the restraining device of the invention in an extended relation;

FIG. 2 is an isometric view of the restraining device of FIG. 1 in a collapsed prepared relation.

DESCRIPTION OF THE PREFERRED EMBODIMENT

Figure 3:
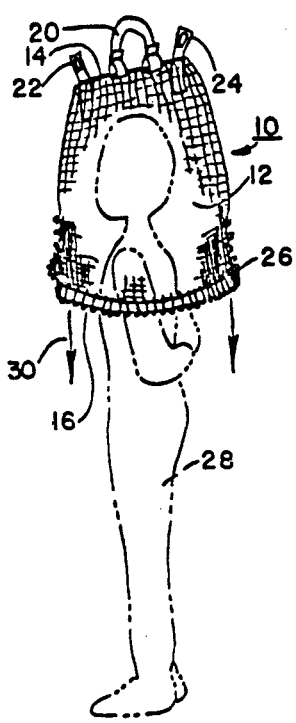
FIGS. 3, 4, 5, and 6 illustrate the sequential steps of applying the restraining device hereof over an individual to be restrained.

In the description which follows, like parts are marked throughout the specification and drawings with the same reference numerals respectively. The drawing figures are not necessarily to scale and in certain views parts may have been exaggerated for purposes of clarity.

Referring initially to FIGS. 1 and 2, the device hereof designated 10 is comprised of a shroud 12 formed of a high-strength open mesh fabric. In a preferred embodiment, shroud 12 is formed of netting material commercially available from builders supply houses as builder's netting. Such netting is characterized as having a tear resistance of at least about 1,500 lbs/ft$^2$.

For these purposes, a selected length of netting is secured at opposite ends to produce a tubular configuration. Upper tube end 14 is closed by threading while lower tube end 16 remains open so as to define access to an internal cavity 18 sized in order to capture even the largest of persons. Also provided at the upper end is a handle 20 and two velcro strips 22 and 24 for maintaining the shroud collapsed in a prepared state when not in use. Surrounding the lower end 14 interweaved through the netting is a loose drawstring 26 for purposes as will be understood. Typically, the diameter of cavity 18 is about thirty inches.

Figure 4:
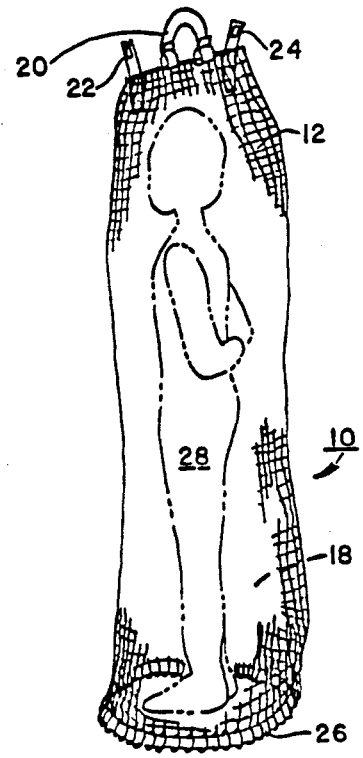
Figure 5:
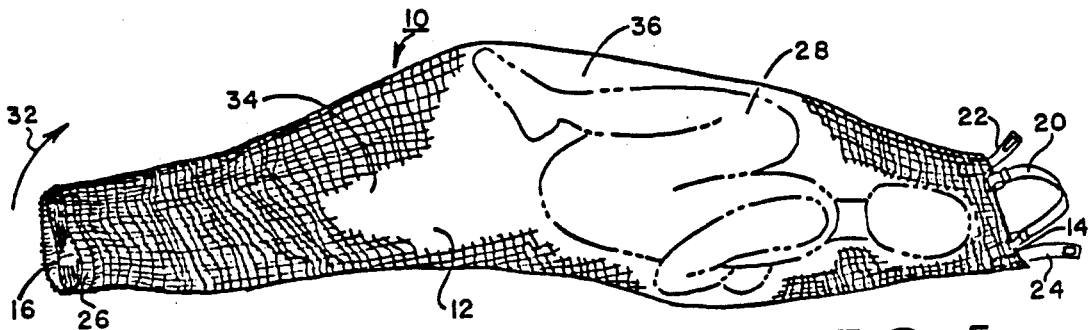
Figure 6:
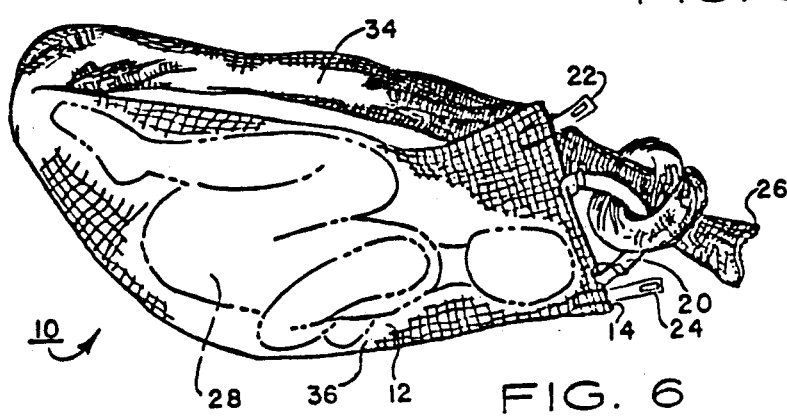

For understanding installation of the restraining device 10 hereof, there is illustrated in FIGS. 3-6 a person 28 shown in phantom and standing erect. In FIG. 3, there is illustrated the previously collapsed restrainer device 10 essentially still partially bunched and being drawn downward from its collapsed state so as to become extended over the person 28 whose arms may or may not have been previously secured together behind his back. As thereshown, the lower open access end 16 is drawn down over the head and toward the floor as indicated by arrows 30 in the course of which shroud 12 is caused to be extended at least the full height of the person 28. On reaching the floor, as illustrated in FIG. 4, the person 28 is completely captured and confined caged within the cavity 18. The excess length 34 at the floor can then be tugged on, forcing the individual into a lying and bending posture as illustrated in FIG. 5.

By tugging the knotted or unknotted segment 34 in an upward direction, as represented by arrow 32, the caged person is caused to be displaced backward toward the normally closed upper end 14. This renders the large lower segment 34 of the shroud freely extending beyond the underend of the person enabling it to be wound in a chordal fashion. Once the respective segments are defined in the foregoing relation, drawstring 26 is drawn tight so as to substantially close lower end 16. The wound lower segment 34 can then be displaced backward over the upper segment 36 and the end 16 thereof knotted about handle 20 in the manner of FIG. 6. The internal dimensions of the cage when in place are controlled by the amount of netting material pulled through the head loop before tying. This allows the application of the net to control the amount of movement available to the restrained person.

By the above description there is disclosed a novel device for physically restraining individuals that are or could potentially become violent. The entire restraining device can be placed in a captive relation about an individual very quickly in a matter of one to two minutes or less and can be done without previously securing the hands and feet. When completely in place, the shroud funnels the arms and legs of the individual into the restraining tube in a capturing manner requiring less effort than before and without the necessity to control the individual's arms and legs in the process. The loop tie-off at the head (FIG. 6) further reduces mobility while enabling the caged person to be readily transported. The device is infinitely flexible and allows bending the restrained individual so as to prevent limb movement in the course of the restraining device being applied. Bending the person in a forward relation as shown, minimizes the likelihood of back injury.

At the same time, the device hereof adequately cages the hands and feet in a barrier of restraint. As a consequence, the person applying the shroud, such as an arresting officer, does not have to impose advance control over the hands and feet of the individual to the degree previously required. This in itself reduces the risk of injury to the arresting officer. The person's hands do not have to be inserted into a sleeve in the manner of a straitjacket or handcuffs and the feet do not have to be tied as has been customary in the past.

By virtue of the relatively light weight and collapsibility of the shroud hereof, it is highly portable and can be readily bagged or otherwise kept in a glove compartment or under the seat of a police squad car. Use of the velcro strips 22 and 24, enable the unit to be collapsed and maintained in a preparedness condition for immediate use. By having drawstring 26 color coded it allows the applier of the restraint to expeditiously locate the bottom hem even in a stressful and hurried situation. Obviously, the device 10 hereof can be made in a variety of sizes to suit different size individuals or can be made sufficiently large for a universal fit of all individuals as is deemed appropriate.

Since many changes could be made in the above construction and many apparently widely different embodiments of this invention could be made without departing from the scope thereof, it is intended that all matter contained in the drawings and specification shall be interpreted as illustrative and not in a limiting sense.

I claim:

1. A body restraining device for a person to be restrained comprising:

a portable shroud means of a foraminous composition and of tubular cross-section for progressive head toward foot slipover placement in a capturing relation about an individual, said shroud means being compressible into a collapsed state and expandable from said state to extend between opposite ends so as to define an internal cavity therein accessed by an opening at one of said ends through which to effect said slipover placement; and p1 said shroud means being of high strength and dimensioned in length and cavity cross-section to exceed the height and width dimensions for an individual to be restrained and effective when emplaced to capture and immobilize the head, arms and feet of the restrained individual against harmful behavior.

2. The body restraining device in accordance with claim 1 in which said shroud means is comprised of a high-strength and relatively limp netting material having one end closed and the other end open for effecting said placement said capture relation about the person to be restrained.

3. The body restraining device in accordance with claim 1 in which said tubular shroud means is of a diameter sufficient to enable caging the person in a bent generally lying posture and of length sufficient with a restrained body disposed in said posture therein enable the open end of said shroud means to be secured.

4. The body restraining device in accordance with claim 2 in which said open end is adapted for placement over the head of the body to be restrained and from which the shroud means is extended downward over the body to at least over the feet.

5. A body restraining device in accordance with claim 2 in which said shroud means is provided with means to maintain said shroud means in a predetermined collapsed relation in preparedness for subsequent use.

6. A method of imposing bodily restraint on a person comprising the stops of:

providing a portable shroud means of foraminous composition and of tubular cross-section said shroud means being compressible into a collapsed state and expandable from said state to extend between ends so as to define an internal cavity therein accessed by an opening at one of said ends;

progressively placing said shroud means via said opening about the body of the person to be restrained in a slipover head to foot capture relation therewith; and securing said shroud means about the captured body so as to immobilize the head, arms and feet of the person against harmful movement.

7. The method of imposing bodily restraint on a person in accordance with claim 6 in which said shroud means comprises a netting material and said step for securing said shroud means comprises the step of securing together the opposite ends of said shroud means.

* * * * *